United States Patent [19]
Kohayakawa et al.

[11] Patent Number: 4,830,483
[45] Date of Patent: May 16, 1989

[54] LASER APPLYING APPARATUS

[75] Inventors: Yoshimi Kohayakawa, Yokohama; Yasuyuki Numajiri, Kawasaki, both of Japan

[73] Assignee: Canon Kabushiki Kaisha, Tokyo, Japan

[21] Appl. No.: 151,168

[22] Filed: Feb. 1, 1988

[30] Foreign Application Priority Data

Feb. 7, 1987 [JP] Japan .................................. 62-027477
Jul. 3, 1987 [JP] Japan .................................. 62-167518
Aug. 31, 1987 [JP] Japan ................................. 62-217132

[51] Int. Cl.$^4$ .............................................. A61B 3/10
[52] U.S. Cl. ...................................... 351/221; 351/205
[58] Field of Search ....................... 351/221, 205, 206; 128/303.1, 395, 630, 633; 350/171

[56] References Cited

U.S. PATENT DOCUMENTS

4,561,436 12/1985 Munnerlyn ........................ 350/171

Primary Examiner—Rodney B. Bovernick
Attorney, Agent, or Firm—Fitzpatrick, Cella, Harper & Scinto

[57] ABSTRACT

A laser applying apparatus provided with a light reflective coupling member having a reflecting coupling member having a reflecting film for reflecting a laser light for medical treatment and transmitting a guide light therethrough provided on the side of a portion to be examined and having a reflecting film for reflecting the transmitted guide light partly provided behind the first-mentioned reflecting film.

15 Claims, 6 Drawing Sheets

PRIOR ART

LASER APPLYING APPARATUS

BACKGROUND OF THE INVENTION

1. Field of the Invention

This invention relates to a laser applying apparatus and a laser treatment apparatus used chiefly in ophthalmic operations or the like, and in particular to a laser applying apparatus provided with an invisible laser for treating an eye to be examined and a visible guide light informing of the application position of said invisible laser.

2. Related Background Art

Figure 10:
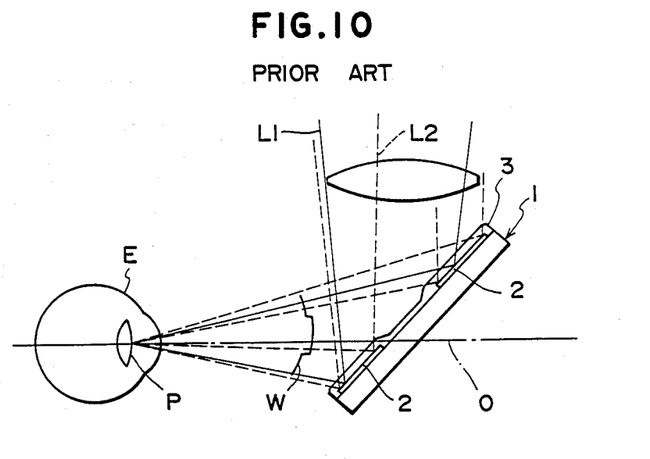
FIG. 10 illustrates an example of the prior art.

Generally, in a laser treatment apparatus of this type, as shown in FIG. 10 of the accompanying drawings, a coupling mirror 1 is obliquely provided on the optic axis 0 of an observation optical system so that an invisible laser light L1 for medical treatment indicated by solid line and a visible guide light L2 indicated by dotted line are reflected toward an eye E to be treated by the coupling mirror 1.

YAG laser light is usually used as the laser light L1 for medical treatment. Also, He-Ne laser light is usually used as the visible guide light L2, but sometimes an incandescent light source is also used. The visible guide light L2 overlaps the laser light L1 for medical treatment when it enters the coupling mirror 1, and is for making it readily discernible whether a focus p is adjusted, and this visible guide light L2 is often divided into two or three light beams.

Heretofore, a guide light reflecting film 2 has been partly divisionally provided on the front surface of the coupling mirror 1 and further, a treatment laser light reflecting film 3 has been generally provided thereon and thus, though slightly, the unevenness by the guide light reflecting film 2 is formed on the surface of the treatment laser light reflecting film 3, and this leads to the problem that the wave surface W of the laser light for medical treatment is disturbed and the light condensation onto the focus P is deteriorated.

U.S. Pat. No. 4,561,436 discloses, as a modification of this, the uniform provision of a treatment YAG laser light reflecting film on the front surface of the mirror and the partial provision thereon of a film reflecting He-Ne laser light which is a guide light, but like the above-described technique, it suffers from the problem that the wave surface of the laser light for medical treatment is disturbed and the light condensation onto the focus P is deteriorated.

SUMMARY OF THE INVENTION

It is an object of the present invention to provide a laser applying apparatus in which any factor which causes the disturbance of the wave surface of an invisible laser light is eliminated and the light condensation onto the focus is improved It is another object of the present invention to provide a laser applying apparatus which is provided with a guide light in addition to YAG laser which is an invisible laser light and in which Ar laser which is a visible laser light can be applied by the use of the same imaging optical system as the YAG laser.

BRIEF DESCRIPTION OF THE DRAWINGS

FIG. 1 (a) shows the construction of a first embodiment of the present invention

DESCRIPTION OF THE PREFERRED EMBODIMENTS

Figure 1A:
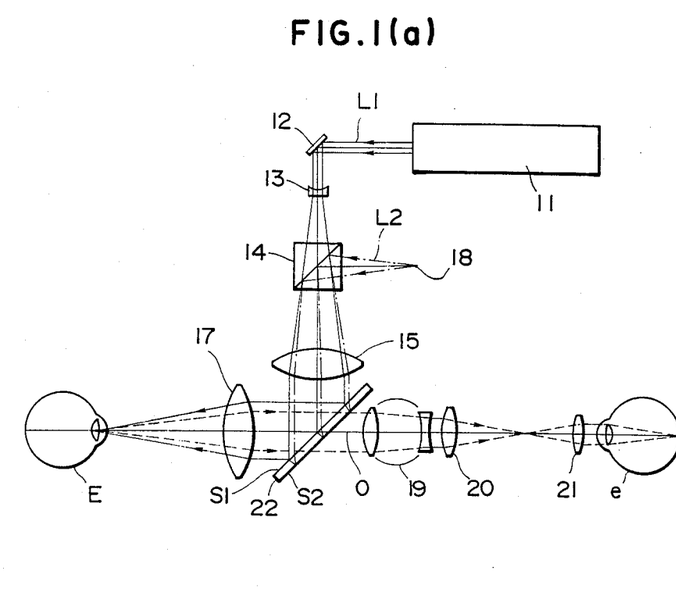

Referring to FIG. 1(a) which shows the construction of a first embodiment of a laser treatment apparatus according to the present invention, the reference numeral 11 designates a laser light source for medical treatment which emits a laser light L1 for medical treatment such as YAG laser light. Along the optic axis of this laser light L1 for medical treatment, there are disposed a deflecting mirror 12, a light beam expanding lens 13, a prism 14, a light beam expanding lens 15 and an obliquely provided coupling mirror 22, and on the reflection side of the coupling mirror 22, an objective lens 17 is disposed in opposed relationship with an eye E to be treated. The front surface S1 of the coupling mirror 22 is coated with an optical thin film for reflecting the laser light L1 for medical treatment, while on the back surface S2 of the coupling mirror 22, an optical thin film for reflecting a visible guide light 12 is provided parallel to the optical thin film provided on the front surface S1. A guide light source 18 which emits a visible guide light L2 such as He-Ne laser light or an incandescent light is provided sideways of the prism 14, and the visible guide light L2 is adapted to coincide with the optical path of the laser light L1 for medical treatment through the prism 14. Further, behind the coupling mirror 22 and on the optic axis 0 passing through the objective lens 17 and the coupling mirror 22, there are arranged a magnification changing lens 19, an imaging lens 20 and an eyepiece 21, and the portion between the objective lens 17 and the magnification changing lens 19 is a parallel light beam portion so that the observing eye e of the operator can look into the eyepiece 21 and observe the eye E to be treated.

The laser light L1 for medical treatment emitted from the laser light source 11 for medical treatment is reflected by the deflecting mirror 12 and is expanded into a parallel beam via the light beam expanding lens 13, the prism 14 and the light beam expanding lens 15, whereafter it is reflected by the front surface S1 of the coupling mirror 22 and is coupled to the optical path of the observation optical system, and is condensed on the eye E to be treated by the objective lens 17.

On the other hand, the visible guide light L2 emitted from the guide light source 18 is reflected by the prism 14, is made into a parallel beam by the light beam expanding lens 15, overlaps the laser light L1 for medical treatment, is reflected by the back surface S2 of the coupling mirror 22 and is condensed at the same position as the laser light L1 for medical treatment by the objective lens 17.

Figure 1B:
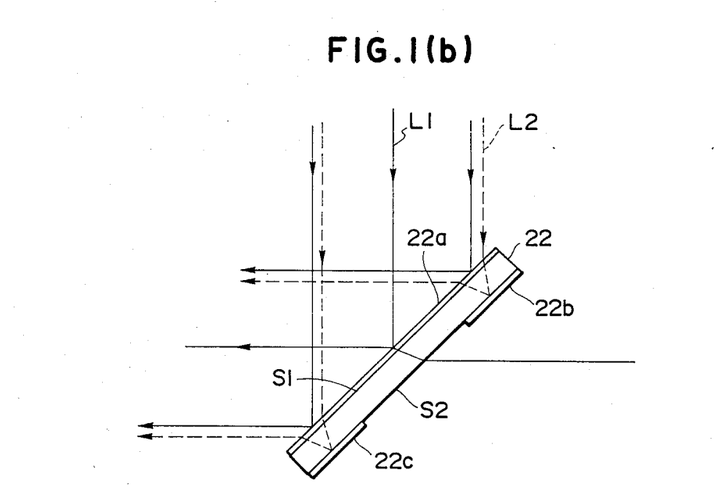
FIG. 1(b) is a side view of a coupling mirror in the first embodiment
Figure 2:
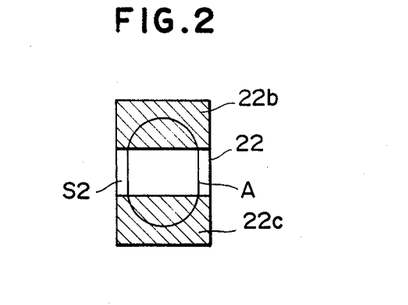
FIG. 2 is a rear view of the coupling mirror in the first embodiment.

FIG. 1(b) is an enlarged cross-sectional view of the coupling mirror 22. The front surface S1 is generally coated with an optical thin film 22a reflecting the invisible laser light L1 for medical treatment and transmitting the visible guide light L2 therethrough, and the opposite side edges of the back surface S2 are partly coated with optical thin films 22b and 22c reflecting the visible guide light L2. That is, as shown in FIG. 2, the optical thin films 22b and 22c are provided on the opposite side edge areas of the back surface S2 indicated by hatching. The optical thin films 22a and 22b, 22c are parallel to each other. Letter A designates an area on which the visible guide light L2 is incident, and the visible guide light L2 reflected by the optical thin films 22b and 22c is separated into two light beams, which become one at the focus position. Also, at a position deviated a little from the focus, the visible guide light L2 is divided in two and therefore, the observing eye e of the operator can clearly discern whether the focus is adjusted. It is to be noted that instead of the visible guide light being divided in two, an optical thin film for reflecting the visible guide light may be provided so as to reflect an annular light beam.

When the visible guide light L2 has become one, the operator causes the laser light source 11 to emit the laser light L1 for medical treatment. Since the front surface S1 of the coupling mirror 22 is generally uniformly coated with an optical thin film transmitting the visible guide light L2 therethrough and reflecting only the laser light L1 for medical treatment, the laser light L1 for medical treatment is reflected by the front surface S1 of the coupling mirror 22 and is condensed at the focus position of the eye E to be treated. The visible guide light L2 is reflected by the back surface S2 of the coupling mirror 22, but it is desirable that as shown in FIG. 1(a), the laser light L1 for medical treatment and the optic axis be made coincident with each other. Since the coupling mirror 22 having a predetermined mirror thickness is located in the parallel beam portion of the observation optical system, even the light beam reflected by the back surface does not create astigmatism, nor the focus position deviates.

Figure 3A:
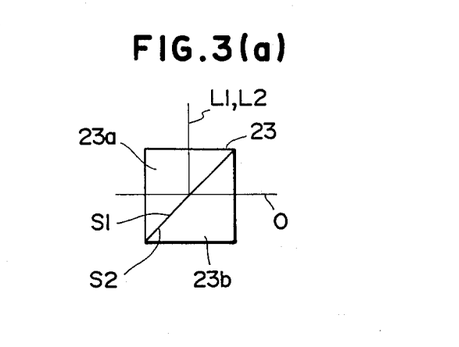
FIG. 3(a) is a side view of a cemented prism used as a modification.
Figure 3B:
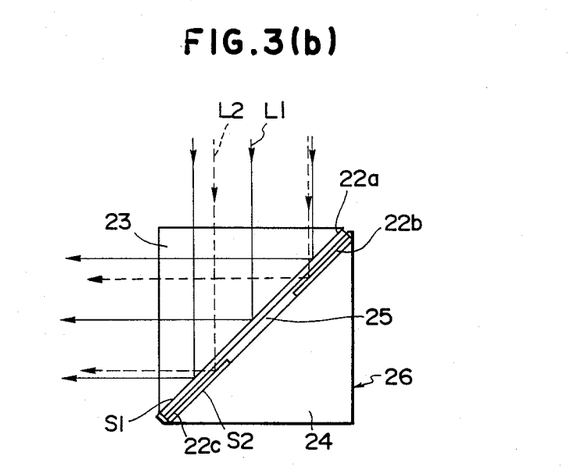
FIG. 3(b) is an enlarged view of the side surface of said cemented prism.

In the above-described embodiment, the coupling mirror 22 is used as a coupling member, but alternatively, a cemented prism 26 as shown in FIGS. 3(a) and (b) may be used instead of the coupling mirror 22 of FIG. 1. In such case, of the two cemented prisms 23 and 24, the joined surface of the prism 23 is uniformly coated with an optical thin film 22a reflecting the laser light L1 for medical treatment and the joined surface of the other prism 24 is coated with optical thin films 22b and 22c divisionally reflecting the visible guide light L2, said optical thin films being parallel to each other. That is, in this case, the front surface S1 which reflects the laser light L1 for medical treatment is the joined surface of the prism 23 and the back surface S2 which reflects the visible guide light L2 is the joined surface of the prism 24, and the visible guide light L2 passes through the adhesive layer 25 between said two surfaces, while the laser light L1 for medical treatment does not pass through the adhesive layer 25. However, this adhesive layer 25 is very thin and therefore, deviation of the light beam hardly occurs and the wave surface of the laser light L1 for medical treatment is not disturbed.

Figure 4:
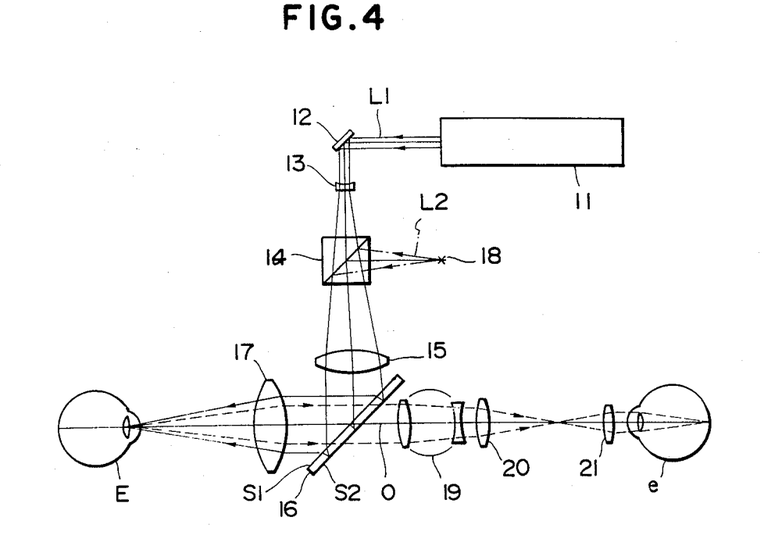
FIG. 4 shows the construction of a second embodiment of the present invention.

FIG. 4 shows a second embodiment of the present invention. In FIG. 4, reference numerals similar to those in FIG. 1 designate similar members. Instead of the coupling mirror 22 in the first embodiment, a coupling mirror 16 having its back surface S2 coated with a thin film for reflecting the laser light for medical treatment is obliquely provided.

Figure 5:
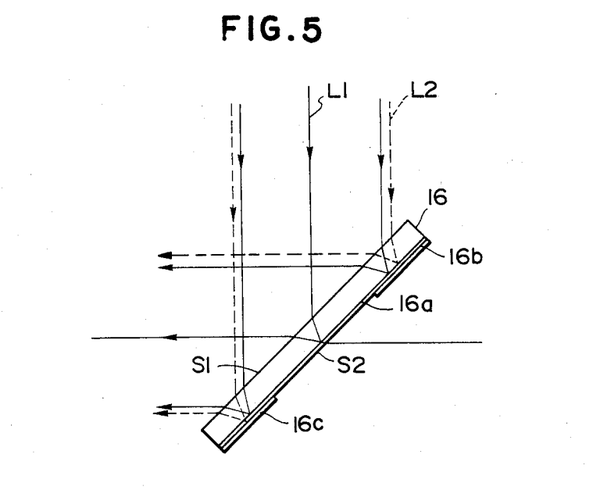
FIG. 5 is a side view of a coupling mirror in the second embodiment.
Figures 6, 7:
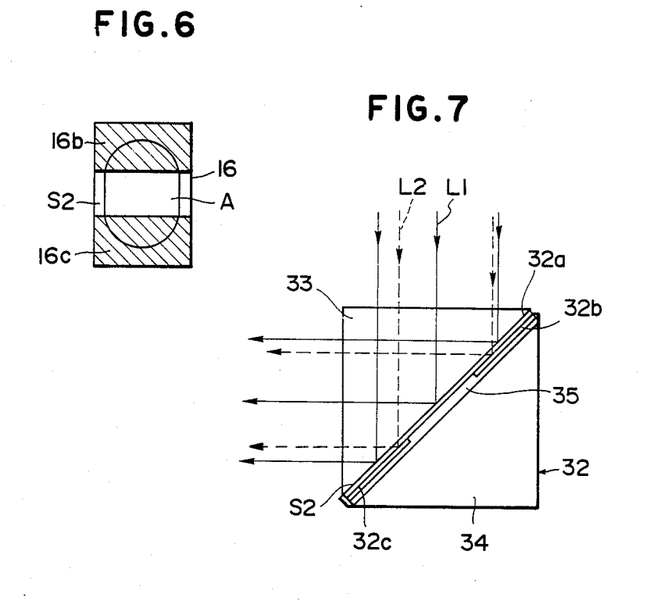
FIG. 6 is a rear view of the coupling mirror in the second embodiment.
FIG. 7 is a side view of a cemented prism used as a modification.

FIG. 5 is an enlarged cross-sectional view of the coupling mirror 16. The back surface S2 of the coupling mirror 16 is coated with an optical thin film 16a as a base layer reflecting the invisible laser light L1 for medical treatment and transmitting the visible guide light L2 therethrough, and the opposite side edges of the back surface S2 is coated with optical thin films 16b and 16c reflecting the visible guide light L2. That is, as shown in FIG. 6, the optical thin films 16b and 16c are provided on the opposite side edge areas of the back surface S2 indicated by hatching. Letter A designates an area on which the visible guide light L2 is incident, and the visible guide light L2 reflected by the optical thin films 16b and 16c is separated into two light beams, which become one at the focus position. Also, at a position deviated a little from the focus, the visible guide light L2 is devided in two and therefore, the observing eye e of the operator can clearly discern whether the focus is adjusted. It is to be noted that instead of the visible guide light being divided in two, an optical thin film for reflecting the visible guide light may be provided so as to reflect an annular light beam.

When the visible guide light L2 has become one, the operator caused the laser light source 11 to emit the laser light L1 for medical treatment. Since the back surface S2 of the coupling mirror 16 is generally uniformly coated with the optical thin film 16a transmitting the visible guide light L2 therethrough and reflecting only the laser light L1 for medical treatment, the laser light L1 for medical treatment which has entered from the front surface S1 of the coupling mirror 16 is reflected by the back surface S2 and is condensed at the focus position of the eye E to be treated. The optical thin film 16a is not affected by the thickness of the optical thin films 16b and 16c and therefore, the laser light L1 for medical treatment reflected by the optical thin film 16a does not have its wave surface disturbed. The visible guide light L2 is reflected by the optical thin films 16b and 16c on the back surface S2 of the coupling mirror 16, but it is desirable that as shown in FIG. 4, the laser light L1 for medical treatment and the optic axis be made coincident with each other. The coupling mirror 16 is located in the parallel light beam portion of the observation optical system and therefore, even the light beam reflected by the back surface does not create astigmatism, nor the focus position deviates.

FIG. 7 shows a modification in which a cemented prism 32, instead of the coupling mirror 16, is used as the coupling optical member. Two prisms 33 and 34 are joined together by an adhesive agent 35. In this cemented prism 32, the thickness of an optical thin film 32a as a base layer can be neglected and therefore, even if the cemented prism is inserted in a convergent light beam, no astigmatism will occur and thus, the cemented prism can also be provided between the objective lens 17 in the parallel light beam portion and the eye E to be treated. That is, the optical thin film 32a reflecting the laser light L1 for medical treatment and transmitting the visible guide light L2 therethrough is generally uniformly provided on the back surface S2 of the prism 33, and optical thin films 32b and 32c reflecting the visible guide light L2 are partly deposited by evaporation as the upper layer of the optical thin film 32a behind the optical thin film 32a.

Figure 8:
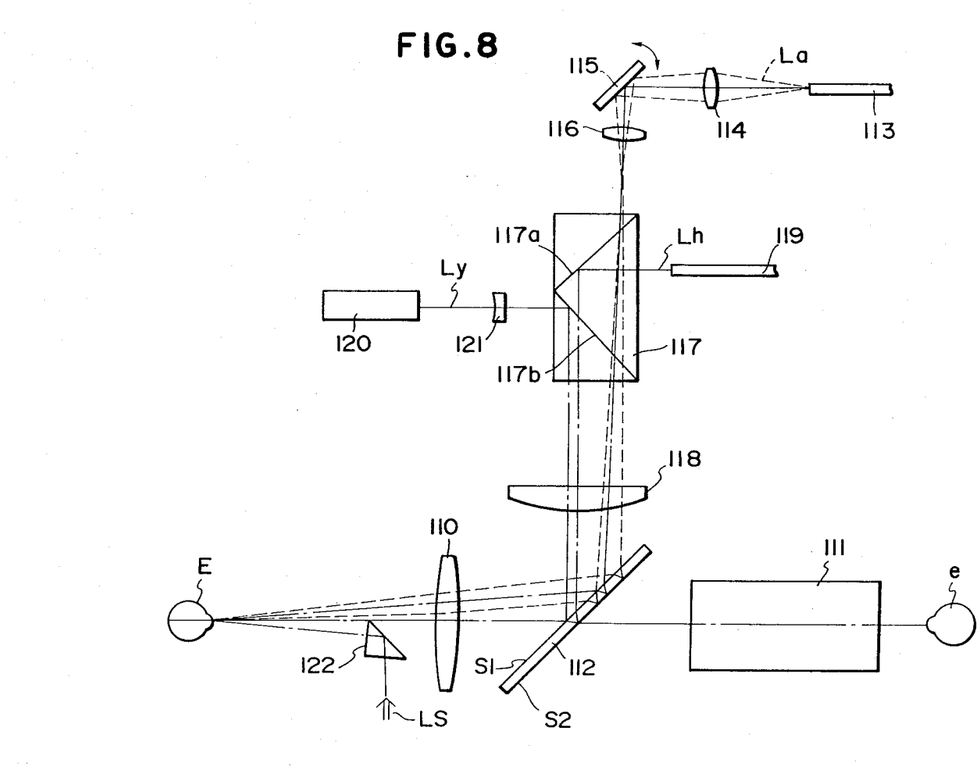
FIG. 8 shows the construction of a third embodiment of the present invention which used Ar laser in addition to YAG laser and He-Ne laser.

FIG. 8 shows a third embodiment of the present invention in which, in contrast with the above-described two embodiments, a laser light for light solidification such as an argon laser can also be used.

Figure 9:
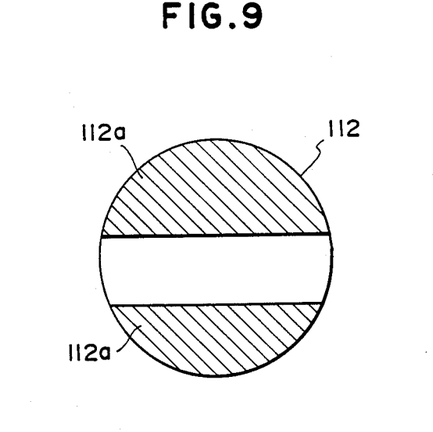
FIG. 9 is a rear view of a coupling mirror in the third embodiment.

In FIG. 8, the letter E designates an eye to be treated and the letter e denotes the eye of the operator. In FIG. 8, a well-known binocular slit lamp observation optical system is constituted by an objective lens 110 and an observation system 111. That is, the observation system 111 is a binocular optical system. A coupling mirror 112 is obliquely provided between the objective lens 110 and the observation system 111 so as to reflect the laser lights toward the eye E to be treated. The laser lights used are YAG laser light Ly for incision, argon laser light La for light solidification, and He-Ne laser light Lh for guide during the use of the YAG laser light Ly. The He-Ne laser light may be replaced by an incandescent lamp light. The front surface S1 of the coupling mirror 112, as in the first embodiment, is coated with an optical thin film for reflecting the invisible light and transmitting the visible light therethrough so that only the YAG laser light Ly is reflected. Visible light reflecting films 112a for reflecting the visible light are provided on the back surface S2 of the coupling mirror 112 at two upper and lower portions indicate by hatching in FIG. 9. A lens 114, a movable mirror 115, a lens 116, a prism 117 for laser, a relay lens 118 and the coupling mirror 112 are disposed along the optical path of the argon laser light La emitted from a fiber 113 for argon laser. A prism 117 for laser which reflects or transmits the laser light therethrough comprises three prisms cemented together, and the reflecting surface 117a thereof is coated with an optical thin film transmitting therethrough the argon laser light La applied from the fiber 113 for argon laser and reflecting the He-Ne laser light Lh entering from a fiber 119 for He-Ne laser. Also, the reflecting surface 117b of the prism 117 is coated with an optical thin film transmitting the argon laser light La and the He-Ne laser light Lh therethrough and reflecting the YAG laser light Ly entering from a YAG laser light oscillator 120 through a concave lens 121. Further, the illuminating light Ls of a slit lamp is adapted to illuminate the eye E to be treated through a movable prism 122 for illumination.

The YAG laser light Ly for incision is applied from the YAG laser light oscillator 120, has its beam diameter expanded by the concave lens 121 for beam expansion, is reflected by the reflecting surface 117b of the prism 117 for laser and is made into a parallel beam by the relay lens 118, whereafter it is reflected by the front surface S1 of the coupling mirror 112 and becomes the same as the optical path of the observation optical system, whereafter it is condensed on the affected part of the eye E to be treated by the objective lens 110. In this case, the prism 122 for illumination which reflects the illuminating light Ls of the slit lamp to the eye E to be treated is moved to a position in which it does not hamper at least the YAG laser light Ly, by a mechanism, not shown.

The He-Ne laser light Lh used for the aim at the affected part during the use of the YAG laser light Ly is directed from an He-Ne laser oscillator, not shown, by the fiber 119 for He-Ne laser, is reflected by the reflecting surface 117a of the prism 117 for laser and becomes parallel to the optical path of the YAG laser light Ly. It is then reflected by the two visible light reflecting films 112a of the coupling mirror 112 and therefore divided into two beams, and the end position of the fiber 119 for He-Ne laser is adjusted so that said two beams intersect each other at the focus position of the YAG laser light Ly, and focusing can be accomplished by searching for the position at which the two beams coincide with each other.

The argon laser light La used for light solidification is directed from an oscillator, not shown, by the fiber 113 for argon laser, is condensed by the lens 114 and is reflected by the movable mirror 115, whereafter it is condensed by the lens 116 and is once imaged, and enters the prism 117 for laser and becomes coincident with the optical path of the He-Ne laser light Lh. However, the position of the optical path and the angle of incidence on the coupling mirror 112 are pre-adjusted by the movable mirror 115 so that the argon laser light La is reflected by only the upper one of the two areas of the visible light reflecting films 112a of the coupling mirror 112 and is condensed on the eye E to be treated.

The argon laser light La may be large in its spot diameter as compared with the YAG laser light Ly and therefore, the reflection area of only the upper visible light reflecting film 112a suffices. Thus, the argon laser light La is applied from obliquely above the optic axis of the observation optical system and it becomes possible to move the prism 122 for illumination up to a position in which it does not hamper the argon laser light La, and observation illumination can be done from a position near the optic axis of the observation optical system. Since light solidification is effected chiefly for the eye fundus, it is desirable that the optic axis of the observation optical system and the optic axis of the observation illumination be coincident with each other. In order to make the focus position of the observation optical system coincident with the applied position of the argon laser light La, it is necessary that the imaging position after the condensation by the lens 116 be made conjugate with the end surface of the fiber 119 for He-Ne laser. Also, if the lens 114 is placed in a conjugate positional relation with the coupling mirror 112, the applied position of the argon laser light La in the eye E to be treated can be changed by changing the angle of the movable mirror 115 without changing the reflected position of the argon laser light La on the coupling mirror 112.

In the present embodiment, selection of the YAG laser light Ly and the argon laser light La has been required, but this may also be accomplished by oscillating only the necessary laser light by electrical change-over, or by intercepting the unnecessary laser light by a shutter. Also, the present embodiment has been described by the use of the YAG laser light Ly and the argon laser light La, but instead of the argon laser light La, other laser light for light solidification such as a krypton laser light or a coloring matter laser light can be used to obtain a similar effect. Also, in the present embodiment, use has been made of the prism 117 for laser comprising three prisms cemented together, but alternatively, three prisms may be disposed discretely or a half-mirror may safely be used.

In the present embodiment, a mirror provided with an invisible laser light reflecting film on the front surface thereof and partly provided with a visible light reflecting film on the back surface thereof as shown in the first embodiment is used as the coupling mirror, but alternatively, use may be made of a mirror provided with an invisible laser light reflecting film on the back surface thereof and partly provided with a visible light reflecting film thereon as in the second embodiment (differing in reference numerals) shown in FIG. 5. Further, use may also be made of the cemented prism as shown in FIGS. 3(a) and (b) or FIG. 7 (differing in reference numerals).

We claim:

1. A laser applying apparatus for use with an eye to be examined, comprising:
   an invisible laser light emitting optical system for emitting an invisible laser light to the eye to be examined;
   a guide light emitting optical system for emitting to the eye to be examined a visible guide light sharing at least a partial optical path with said invisible laser light for indicating the position of said invisible laser light;
   an observation optical system for observing the eye to be examined; and
   a coupling member provided at a position for optically coupling said invisible laser light emitting optical system and said guide light emitting optical system to said observation optical system, said coupling member including a surface provided obliquely with respect to the optical axis of said coupling member, said surface including a first light reflecting film provided as a coating thereon for reflecting said invisible laser light to the eye to be examined and for transmitting said guide light therethrough, said coupling member further including a second light reflecting film lying behind said first light reflecting film as viewed from the eye to be examined and provided as coating on a predetermined area outside the optical path of said observation optical system, said second light reflecting film for reflecting said guide light to the eye to be examined.

2. A laser applying apparatus according to claim 1, wherein said invisible laser light emitting optical system includes means for emitting YAG laser light.

3. A laser applying apparatus according to claim 1, wherein said guide light emitting optical system includes means for emitting He-Ne laser light.

4. A laser applying apparatus according to claim 1, wherein said guide light emitting optical system includes means for emitting an incandescent light.

5. A laser applying apparatus according to claim 1, wherein said coupling member is provided with first and second surfaces provided obliquely with respect to the optic axis in succession as viewed from the eye to be examined, said first surface being coated with said first light reflecting film, said second surface being partly coated with said second light reflecting film.

6. A laser applying apparatus according to claim 1, wherein said coupling member is provided with a first surface opposed to the eye to be examined and a second surface contrary to the eye to be examined, said second surface being coated with said first light reflecting film, said first light reflecting film being partly coated with said second light reflecting film.

7. A laser applying apparatus according to claim 1, wherein said coupling member is a coupling mirror.

8. A laser applying apparatus according to claim 1, wherein said coupling member is a cemented prism.

9. A laser applying apparatus according to claim 1, wherein said coupling member is in a parallel light beam in said observation optical system, said parallel light beam being images on the eye to be examined by an objective lens.

10. A laser applying apparatus according to claim 1, wherein said second light reflecting film is provided as coating on at least two spatially separated areas.

11. A laser applying apparatus according to claim 1, wherein said first light reflecting film and said second light reflecting film are provided parallel to each other.

12. A laser applying apparatus for use with an eye to be examined, comprising:
   an invisible laser light emitting optical system for emitting an invisible laser light to the eye to be examined;
   a visible laser light emitting optical system for emitting to the eye to be examined a visible laser light sharing at least a partial optical path with said invisible laser light;
   a guide light emitting optical system for emitting to the eye to be examined a visible guide light sharing at least a partial optical path with said invisible laser light and said visible laser light for indicating the position of application of the invisible laser light on the eye to be examined;
   an observation optical system for observing the eye to be examined; and
   a coupling member provided at a position for optically coupling said invisible laser light emitting optical system, said visible laser light emitting optical system and said guide light emitting optical system to said observation optical system, said coupling member including a surface provided obliquely with respect to the optical axis of said coupling member, said surface including a first light reflecting film provided as a coating thereon for reflecting said invisible laser light to the eye and transmitting said visible laser light and said guide light therethrough, said coupling member further including a second light reflecting film lying behind said first light reflecting film as viewed from the eye to be examined and provided at a predetermined area outside the optical path of said observation optical system, for reflecting said visible laser light and said guide light to the eye to be examined.

13. A laser applying apparatus according to claim 12, wherein said visible laser light emitting optical system includes means for emitting Ar laser light.

14. A laser applying apparatus according to claim 12, wherein the eye to be examined is illuminated by a slit illuminating system further including a slit illuminating means for illuminating the eye to be examined.

15. A laser applying apparatus according to claim 14, wherein said slit illuminating means includes means for providing a light beam that passes through one side of the optical path between said coupling member and the eye to be examined, and said visible laser light emitting optical system includes means for directing the visible laser light through the other side.

* * * * *

UNITED STATES PATENT AND TRADEMARK OFFICE
CERTIFICATE OF CORRECTION

PATENT NO. : 4,830,483

DATED : May 16, 1989

INVENTOR(S) : Yoshimi Kohayakawa, et al.

It is certified that error appears in the above-identified patent and that said Letters Patent is hereby corrected as shown below:

IN THE SPECIFICATION:

COLUMN 1

Line 29, "focus p" should read --focus P--.
　　Line 68, "invention" should read --invention.--.

COLUMN 2

Line 2, "embodiment" should read --embodiment.--.
　　Line 18, "used" should read --uses--.
　　Line 42, "visible guide light 12" should read --visible guide light L2--.

COLUMN 3

Line 48, "nor the focus position deviates." should read --and the focus position does not deviate.--.

COLUMN 4

Line 26, "devided" should read --divided--.
　　Line 33, "caused" should read --causes--.
　　Line 55, "nor the focus position deviates." should read --and the focus position does not deviate.--

COLUMN 5

Line 30, "indicate" should read --indicated--.

UNITED STATES PATENT AND TRADEMARK OFFICE
CERTIFICATE OF CORRECTION

PATENT NO. : 4,830,483

DATED : May 16, 1989

INVENTOR(S) : Yoshimi Kohayakawa, et al.

It is certified that error appears in the above-identified patent and that said Letters Patent is hereby corrected as shown below:

IN THE CLAIMS:

COLUMN 7

Line 29, "optical axis" should read --optic axis--.

COLUMN 8

Line 8, "images" should read --imaged--.
Line 39, "optical axis" should read --optic axis--.

Signed and Sealed this

Eighth Day of May, 1990

Attest:

HARRY F. MANBECK, JR.

Attesting Officer

Commissioner of Patents and Trademarks